United States Patent [19]

Gräwinger et al.

[11] 4,335,123

[45] Jun. 15, 1982

[54] 1-ACYL-8-(3-AMINO-2-HYDROXYPROPOX-Y)-1,2,3,4-TETRAHYDROQUINOLINES, COMPOSITIONS AND USE

[75] Inventors: Otto Gräwinger, Frankfurt am Main; Thomas Raabe, Rodenbach; Rudi Beyerle, Frankfurt am Main; Josef Scholtholt, Hanau-Mittelbuchen; Rolf-Eberhard Nitz, Frankfurt am Main, all of Fed. Rep. of Germany

[73] Assignee: Cassella Aktiengesellschaft, Frankfurt am Main, Fed. Rep. of Germany

[21] Appl. No.: 178,475

[22] Filed: Aug. 15, 1980

[30] Foreign Application Priority Data

Aug. 28, 1979 [DE] Fed. Rep. of Germany ....... 2934609

[51] Int. Cl.[3] .................... A61K 31/54; A61K 31/47; C07D 215/26; C07D 417/12
[52] U.S. Cl. .............................. 424/246; 424/248.51; 424/248.54; 424/250; 424/258; 544/128; 544/58.6; 544/363; 546/165
[58] Field of Search ...................... 544/128, 58.6, 363; 546/165; 424/246, 248.54, 250, 258, 248.51

[56] References Cited

U.S. PATENT DOCUMENTS 3,056,792 10/1962 Geschickter et al. ............... 546/165
3,444,173 5/1969 Goldman ............................. 546/165

FOREIGN PATENT DOCUMENTS 2362278 6/1974 Fed. Rep. of Germany .
1198123 12/1959 France .

OTHER PUBLICATIONS

Crowther, A. F., et al., "β-Adrenergic Blocking Agents, 12, Heterocyclic Compounds Related to Propanolol", *Journal of Medicinal Chemistry*, vol. 15, No. 3, 260-266, 1972.

*Primary Examiner*—Robert W. Ramsuer
*Attorney, Agent, or Firm*—Berman, Aisenberg & Platt

[57] ABSTRACT

A 1-acyl-8-[2,3-epoxypropoxy]- and/or 1-acyl-8-[3-halo-2-hydroxypropoxy]-1,2,3,4-tetrahydroquinoline are reacted with primary and secondary amines to obtain corresponding physiologically-active 1-acyl-8-[3-amino-2-hydroxypropoxy]-1,2,3,4-tetrahydroquinolines and pharmacologically-acceptable acid-addition salts thereof. These compounds are useful as such or in conventional medicament compositions for treating those afflicted with heart ailments and/or hypertension.

17 Claims, No Drawings

1-ACYL-8-(3-AMINO-2-HYDROXYPROPOXY)-1,2,3,4-TETRAHYDROQUINOLINES, COMPOSITIONS AND USE

TECHNICAL FIELD

Tetrahydroquinoline derivatives have antiarrhythmic and hypotensive activities which make them useful for treating heart disorders and hypertension.

SUMMARY OF THE INVENTION

1-Acyl-8-[3-amino-2-hydroxypropoxy]-1,2,3,4-tetrahydroquinolines (A) and their acid-addition salts have therapeutically-useful antiarrhythmic and hypotensive activities. They are prepared, e.g., by reacting 1-acyl-8-[2,3-epoxypropoxy]- and/or 1-acyl-8-[3-halo-2-hydroxypropoxy]-1,2,3,4-tetrahydroquinoline with a primary or secondary amine or cycloimine. Pharmacologically-acceptable compounds (A) and their pharmacologically-acceptable acid-addition salts, per se or in conventional medicament compositions (e.g. as standard dosage forms), are administered to humans afflicted with cardiac disorders and/or hypertension.

Compounds (A), their acid-addition salts, their novel intermediates, their synthesis, their medicament compositions, their dosage forms and their use in treating patients are different aspects of the subject invention.

DETAILS

The invention relates more specifically to pharmacologically-valuable derivatives of tetrahydroquinoline of the formula

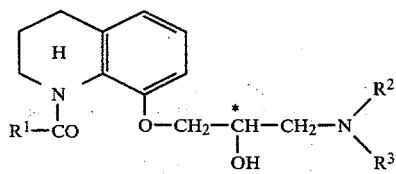
(I)

[wherein $R^1$ denotes alkyl, phenyl, substituted phenyl or heteroaryl; and each of $R^2$ and $R^3$, independently, denotes hydrogen (—H) or alkyl, or $R^2$ and $R^3$, together with the nitrogen atom to which both are bound, form a heterocyclic ring, optionally via a further hetero-atom grouping] and to acid-addition salts thereof.

The compounds of formula I have an asymmetric carbon atom (marked with an asterisk) in the alkanolamine side chain and therefore exist in racemic and optically-active forms. In the context of the present invention, compounds of formula I include stereoisomers and optically-active compounds as well as mixtures thereof, especially the racemate.

The alkyl radicals represented by $R^1$ have, in particular, from 1 to 5 C atoms. Examples of suitable lower alkyl radicals represented by $R^1$ are methyl, ethyl, n-propyl, isopropyl, n-butyl, isobutyl, sec.-butyl, tert.-butyl, n-pentyl and isopentyl. The substituted phenyl radical represented by $R^1$ has, e.g., one, two or three substituents. of suitable substituents are lower alkyl and lower alkoxy radicals, particularly those with from 1 to 3 C atoms; halo, particularly fluoro or chloro; and trifluoromethyl. Examples of suitable substituted phenyl radicals represented by $R^1$ are 2-, 3- or 4-methyl, -ethyl-, -n-propyl- or -isopropyl-phenyl; 2-, 3- or 4-methoxy-, -ethoxy- or -n-propoxy-phenyl; 3,5-dimethyl-phenyl; 3,4,5-trimethylphenyl; 3,5-dimethoxyphenyl; 3,4,5-trimethoxyphenyl; 2-, 3- or 4-chloro- or -fluoro-phenyl; and 2-, 3- or 4-trifluoromethylphenyl. Preferred substituted phenyl radicals are those having one lower alkyl, halo or trifluoromethyl substituent or one, two or three lower alkoxy substituents. The heteroaryl radicals represented by $R^1$ are, in particular, 5-membered or 6-membered heteroaryl radicals in which the sole ring heteroatom is nitrogen, oxygen or sulfur, for example thienyl, furyl, pyrrolyl and, preferably, pyridyl.

$R^2$ and $R^3$, independently of one another, denote hydrogen (—H) or an alkyl radical, in particular with from 1 to 4 C atoms, which is preferably branched. Examples of suitable lower alkyl radicals are methyl, ethyl, n-propyl, n-butyl, sec.-butyl and, preferably, isopropyl, isobutyl and tert.-butyl. $R^2$ and $R^3$, together with the nitrogen atom to which both are bound, alternatively form a heterocyclic ring, optionally via a further hetero-atom grouping, for example —O—, —S— or —NH—. This heterocyclic ring preferably has 5 or 6 members. Examples of such meanings of $R^2$ and $R^3$ are: piperidino, 1-piperazinyl, morpholino, thiomorpholino, 1-imidazolidinyl, 2-pyrazolidinyl, 1-oxazolidinge, 1-thiazolidinyl and 1-pyrrolidinyl.

Compounds of formula I and acid-addition salts thereof, in which $R^2$ represents hydrogen and $R^3$ denotes the isopropyl or tert.-butyl group, are usually preferred.

To prepare the compounds of formula I, a compound of formula II

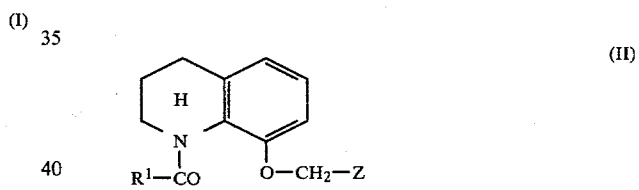
(II)

(wherein Z represents

—CH—CH$_2$ or —CH—CH$_2$—Hal,
  \ /              |
   O              OH and Hal denotes a halogen atom, particularly chloro or bromo) is reacted with an amine of the formula $R^2$—NH—$R^3$ (III)

and, if appropriate, the resulting compound is reacted with an acid to obtain an acid-addition salt.

Instead of using a single compound of formula II, a mixture of a compound of formula IIa and a compound of formula IIb

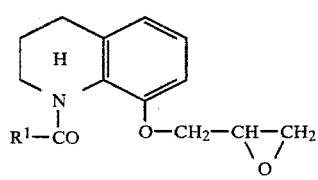
(IIa)

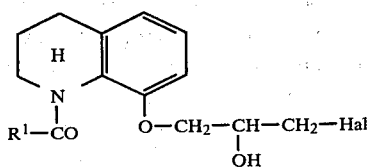 (IIb)

(which are substituted in the same manner with respect to R¹) are optionally used. Hal in formula IIb denotes a halogen atom, particularly chloro or bromo.

The reaction of compounds of formulae II and III is usually carried out in a suitable solvent or dispersing agent in which the reactants are dissolved or suspended. Examples of such solvents or dispersing agents are water; aromatic hydrocarbons, such as benzene, toluene and xylene; ketones, such as acetone and methyl ethyl ketone; halogenated hydrocarbons, such as chloroform, carbon tetrachloride, chlorobenzene and methylene chloride; ethers, such as tetrahydrofuran and dioxane; sulfoxides, such as dimethylsulfoxide; and tertiary acid amides, such as dimethylformamide and N-methylpyrrolidone. The solvents used are, in particular, polar solvents, such as alcohols. Examples of suitable alcohols are methanol, ethanol, isopropanol and tert.-butanol and the like. Lower alkanols with from 1 to 4 C atoms are preferred. The reaction is carried out at temperatures from 20° C. to the reflux temperature of the solvent or dispersing agent used. The reaction frequently proceeds at temperatures of 60° to 100° C. It may be expedient to employ the amine of formula III in up to a 10-fold molar excess, or in some cases even a higher molar excess, and/or to add the reactants of formula II (in dissolved or suspended form) to the dissolved or suspended amine of formula III. The molar ratio between the compounds of formulae II and III is, therefore from 1:1 to 1:10 or even higher. When a compound of formula IIb is present, the reaction is alternatively carried out in the presence of an acid-binding agent, such as potassium carbonate, sodium carbonate, triethylamine and the like. When no acid-binding agent is present, the hydrohalides of the compounds of formula I are usually obtained.

Inorganic and organic acids are suitable for the formation of acid-addition salts with the compounds of formula I. Examples of suitable acids are hydrogen chloride, hydrogen bromide, naphthalene-1,5-disulfonic acid, phosphoric acid, nitric acid, sulfuric acid, oxalic acid, lactic acid, tartaric acid, acetic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, nicotinic acid, methanesulfonic acid, p-toluenesulfonic acid, citric acid and adipic acid. Pharmaceutically-acceptable acid-addition salts are preferred. The acid-addition salts are conventionally obtained by combining the components appropriately in a suitable diluent or dispersing agent. Acid-addition salts which contain 1 mol of acid, as the anion, per mol of base of formula I are thereby usually obtained. When R¹ denotes a heteroaryl radical with a basic N atom, such as the pyridyl group, and/or R² and R³ form a heterocyclic ring with another —NH— group, salt formation can also lead to acid-addition slts which contain 2 or 3 mols of acid (as the anion) per 1 mol of base of formula I.

As those acid-addition salts which are not pharmacologically-acceptable are readily converted (by well established processes) into those which are, all acid-addition salts are useful and are within the scope of this invention.

The starting compounds of formula II are prepared, e.g., by reacting a compound of the formula

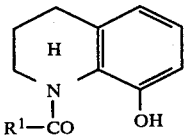 (IV)

with an epihalohydrin, appropriately with epichlorohydrin or epibromohydrin. A compound of formula II or a mixture of compounds of formulae IIa and IIb is thereby formed, depending on the reaction conditions. The reaction product formed is optionally isolated for its further reaction with compound III, but it is alternatively further reacted directly, i.e. without isolation.

To prepared compounds of formula IV, 8-hydroxy-1,2,3,4-tetrahydroquinoline V is reacted with acylating agents of formula VI

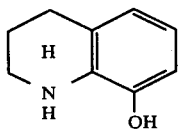 (V)

R¹—CO—X, (VI)

wherein X represents halogen (particularly chloro or bromo) or the radical R¹—CO—O—. Compounds of formulae V and VI are either known or are prepared from available starting materials by established and conventional processes.

Optically-active forms of the tetrahydroquinolines of formula I are obtained by resolution of the corresponding racemic tetrahydroquinolines of formula I by means of customary methods, for example by reacting the racemate of a compound of formula I with an optically-active acid, following this reaction by fractional crystallization of the resulting diastereomeric salt mixture from a suitable diluent or solvent, such as ethanol, and finally liberating the optically-active tetrahydroquinoline from the salt by means of a base. Optically-active compounds of formula I are also obtained by using optically-active starting compounds IIb. These optically-active starting compounds are obtained in a known manner from the optically-inactive compounds IIb by resolving the racemate.

The compounds of formula I according to the invention and pharmaceutically-acceptable acid-addition salts thereof have valuable pharmaceutical properties. In particular, they have powerful antiarrhythmic and hypotensive actions. They are useful for treating heart complaints and heart diseases, such as cardiac arrhythmias, and also for treating hypertension. The tetrahydroquinolines according to the invention are administered enterally or parenterally to humans afflicted with the noted disorders; they are administered by themselves, as mixtures with one another or in pharmaceutical formulations which contain, as the active constituent, an effective dose of at least one tetrahydroquinoline according to the invention (or pharmaceutically-acceptable acid-addition salt thereof) in addition to customary pharmaceutically-acceptable excipients and additives. Examples of suitable excipients are water, vegetable oils, starch, gelatin, lactose, magnesium stearate, waxes, petroleum jelly and the like. Additives which can be used are, for example, wetting agents, disintegrating agents, preservatives and the like.

The pharmaceutical preparations are, for example, in the form of tablets, capsules, aqueous or oily solutions or suspensions, emulsions, injectable aqueous or oily solutions or suspensions, dispersible powders or aerosol mixtures. The pharmaceutical preparations optionally additionally contain, besides compounds of formula I, one or more other pharmaceutically-active substances, for example tranquillizers, such as Luminal, Meprobamate, chloropromazines and benzodiazepine sedatives (e.g. diazepam or chlorodiazepoxide); vasodilators, such as glycerol trinitrate, pentaerythritol tetranitrate and carbochromene; diuretic agents, such as chlorothiazide; heart tonics, such as digitalis preparations; hypotensive agents, such as Rauwolfia alkaloids and guanethidine; bronchodilators and sympathomimetic agents, such as isoprenaline, ociprenaline, adrenalin and ephedrine; α-adrenergic blocking agents, such as phentolamine; β-adrenergic blocking agents, such as propanolol; and agents which stabilize the cardiac membrane (antiarrhythmic agents), such as quinidine and catechol amines (e.g. noradrenalin).

The preparation of the compounds of formula I is illustrated in more detail by the following examples:

EXAMPLE 1

1-Nicotinoyl-8-[3-isopropylamino-2-hydroxypropoxy]-1,2,3,4-tetrahydroquinoline

A solution of 23 g of 1-nicotinoyl-8-[2,3-epoxyprop-1-oxy]-1,2,3,4-tetrahydroquinoline of the formula

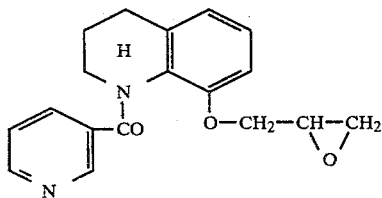

in 100 ml of ethanol is added dropwise to a solution of 60 ml of isopropylamine in 100 ml of ethanol at room temperature (20° C.) in the course of 30 minutes, while stirring. The mixture is then boiled under reflux for 8 hours, and the solution is subsequently concentrated in a waterpump vacuum. The oil which remains is dissolved in 100 ml of ethyl acetate, and the solution is shaken twice with 30 ml of 2 N hydrochloric acid each time. The combined aqueous hydrochloric acid extracts are then brought to pH 11 with 2 N sodium hydroxide solution and extracted twice with 50 ml of ethyl acetate each time. The combined ethyl acetate extracts are dried and then concentrated under a waterpump vacuum. A solid residue remains and is recrystallized once from ethyl acetate and then dissolved again in ethyl acetate, and a solution of naphthalene-1,5-disulfonic acid in ethyl acetate is added. The salt of naphthalene-1,5-disulfonic acid (which precipitates) is filtered off and recrystallized twice from water. 1-Nicotinoyl-8-[(3-isopropylamino)-2-hydroxypropoxy]-1,2,3,4-tetrahydroquinoline naphthalene-1,5-disulfonate is thus obtained as the monohydrate of the formula

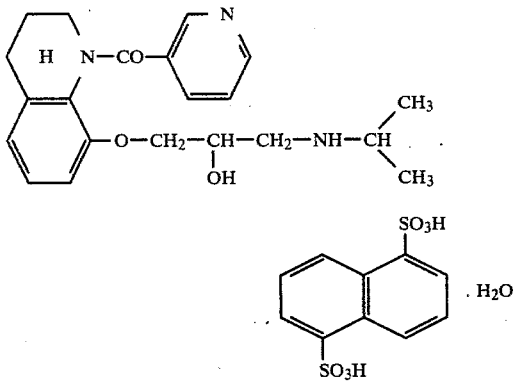

Melting point: 292° C. (decomposition)
Analysis: ($C_{31}H_{37}N_3O_{10}S_2$)
calculated: C 55.1 H 5.5 N 6.2 O 23.7 S 9.5
found: 55.1 5.8 5.9 23.5 9.7
Yield: 76% of theory.

In order to obtain the free base, the naphthalene-disulfonate is dissolved in water, the aqueous solution is brought to pH 10.5 with dilute sodium hydroxide solution and the mixture is extracted twice with ethyl acetate. The ethyl acetate extracts are then concentrated under a waterpump vacuum, and the residue is recrystallized from ethyl acetate. 1-Nicotinoyl-8-[(3-isopropylamino)-2-hydroxypropoxy]-1,2,3,4-tetrahydroquinoline is thus obtained as the free base.

Melting point: 122° C.
Analysis: ($C_{21}H_{27}N_3O_3$)
calculated: C 68.3 H 7.3 N 11.4 O 13.0
found: 68.2 7.5 11.4 12.9

The 1-nicotinoyl-3-[(2,3-epoxyprop-1-oxy]-1,2,3,4-tetrahydroquinoline used as the starting material is prepared as follows:

40 g of 1-nicotinoyl-8-hydroxy-1,2,3,4-tetrahydroquinoline

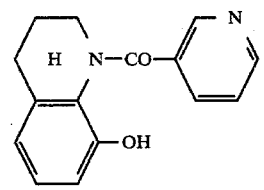

are dissolved in 300 ml of dimethylformamide and 21 g of potassium tert.-butylate are then added at 5° C., while stirring. The mixture is stirred at 5° C. for 20 minutes, 66 g of epichlorohydrin are then added dropwise at this temperature, while stirring, and the mixture is then allowed to warm to room temperature and is subsequently stirred for 20 hours. Thereafter, the mixture is concentrated under a waterpump vacuum. The oil which remains is dissolved in water/toluene; the toluene phase is separated off, washed twice with dilute aqueous sodium hydroxide solution and once with water, dried and concentrated under a waterpump vacuum. A solid residue, which can be reacted directly with isopropylamine to give 1-nicotinoyl-8-[(3-isopropylamino)-2-hydroxypropoxy]-1,2,3,4-tetrahydroquinoline, remains. The 1-nicotinoyl-8-hydroxy-1,2,3,4-tetrahydroquinoline used as the starting material is obtained in the customary manner by reacting 8-hydroxy-1,2,3,4-tetrahydroquinoline with nicotinic acid chloride hydrochloride in toluene at room temperature in the presence of triethylamine. (Melting point: 122° C.).

EXAMPLE 2

1-Benzoyl-8-[3-morpholino-2-hydroxypropoxy]-1,2,3,4-tetrahydroquinoline

A solution of 5 g of 1-benzoyl-8-[2,3-epoxyprop-1-oxy]-1,2,3,4-tetrahydroquinoline in 100 ml of ethanol is added dropwise to a solution of 1.7 g of morpholine in 10 ml of ethanol at room temperature, and the mixture is then heated under reflux for 2 hours. It is then concentrated under a waterpump vacuum. An oil, which solidifies after a short time, remains. After recrystallization of the solid from isopropanol, 1-benzoyl-8-[3-morpholino-2-hydroxypropoxy]-1,2,3,4-tetrahydroquinoline of the formula

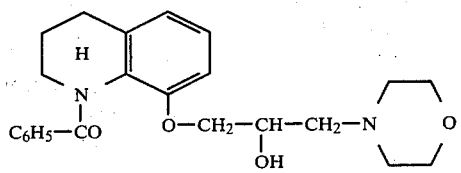

is obtained.
Melting point: 120° C.
Analysis: ($C_{23}H_{28}N_2O_4$)
calculated: C 69.7  C 7.1  N 7.1  O 16.2
found: 69.5  7.3  7.2  16.0
Yield: 83% of theory The 1-benzoyl-8-[2,3-epoxyprop-1-oxy]-1,2,3,4-tetrahydroquinoline used as the starting material is prepared, e.g., as follows: 15 g of 1-benzoyl-8-hydroxy-1,2,3,4-tetrahydroquinoline are dissolved in a solution of 3 g of sodium hydroxide in 350 ml of water at room temperature.

6.5 g of epichlorohydrin are then added dropwise at room temperature, and the mixture is subsequently stirred at room temperature for 24 hours. The precipitate (which has separated out) is then filtered off. The product is subsequently reacted with morpholine without further purification.

The compounds

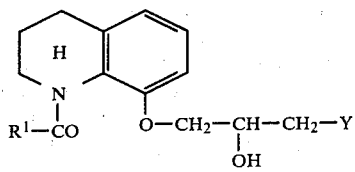

in the following Table are prepared according to the procedures of Examples 1 and 2:

| $R^1$ | Y | Melting point |
|---|---|---|
| phenyl | —NH—CH(CH₃)₂ | 155° C. (Hydrochloride) |
| phenyl | —NH—C(CH₃)₃ | 163° C. |
| 3-CF₃-phenyl | —NH—C(CH₃)₃ | 116° C. |
| phenyl | piperidino (—N with H) | 110° C. |
| —C₄H₉(n) | —NH₂ | 95° C. |
| 3,4,5-trimethoxyphenyl (OCH₃, OCH₃, OCH₃) | —NH—CH(CH₃)₂ | 215° C. (Hydrochloride) |
| —CH₃ | —NH—C(CH₃)₃ | 198° C. (Hydrochloride) |
| —C₅H₁₁(n) | piperidino (—N with H) | 121° C. |
| —C(CH₃)₃ | —NH—C₄H₉(n) | 182° C. (Hydrochloride) |
| 4-Cl-phenyl | —NH—C₂H₅ | 203° C. (Hydrochloride) |
| 4-C₂H₅-phenyl | —N(C₂H₅)₂ | 186° C. (Hydrochloride) |
| 2-furyl | —NH—C₃H₇(n) | 119° C. |
| 2-thienyl | morpholino (—N O ring) | 194° C. (decomposition) (Hydrochloride) |
| pyridyl | —N(CH₃)₂ | 128° C. |

The pharmaceutical formulations contain, e.g., 0.1 to 50 mg and, preferably, from 0.5 to 10 mg/dose. The daily dosage range per kilogram of bodyweight is, e.g., 0.001 to 1 mg, preferably 0.005 to 0.2 mg.

EXAMPLE 3

Sugar-coated pills can be prepared according to the following formulation:

| | |
|---|---|
| 1-Nicotinoyl-8-[3-isopropylamino-2-hydroxy-propoxy]-1,2,3,4-tetrahydroquinoline | 1 mg |
| Cornstarch | 100 mg |
| Lactose | 60 mg |
| Sec. calcium phosphate | 30 mg |
| Soluble starch | 3 mg |

EXAMPLE 4

Tables can be prepared according to the following formulation:

| | |
|---|---|
| 1-Nicotinoyl-8-[3-isopropylamino-2-hydroxy-propoxy]-1,2,3,4-tetrahydroquinoline | 2 mg |
| Lactose | 60 mg |
| Cornstarch | 30 mg |
| Soluble starch | 4 mg |
| Magnesium stearate | 4 mg |
| | 100 mg |

The antiarrythmic action of the compounds of the instant invention was tested on anesthesized rats and on dogs poisoned with strophantin.

Methodology for the anesthesized rats:

Male rates (300–500 g) under urethane anesthesis were given an intravenous infusion of aconitine at a dosage of 5 µg/kg/min while simultaneoulsy recording an electrocardiogram. To measure the antiarrythmic action the aconitine doses administered until the occurrence of extrasystoles, ventricular tachycardia, ventricular fibrillation and exitus were used. The values obtained are given in Table 1.

Methodology for the dogs poisoned with strophantin:

Dogs under Nembutal anesthesis were given infusions of strophantin-K (3 µg/kg/min) for 40 minutes until the occurrence of stable arrythmias. 10 minutes after the end of the infusions intravenous and intraduodenal administration of the test substances was effected. Normalisation of the electrocardiogram for at least 10 minutes was judged as a positive condition. The values obtained are given in Table 2.

TABLE 1

| Substances Dose 10.0 mg/kg, intravenously | Amount of Aconitine in µ g/100 g of Rat Bodyweight until the Occurrence of | | | |
|---|---|---|---|---|
| | Extrasystoles | Ventricular Tachycardia | Ventricular Fibrillation | Exitus |
| 1-Nicotinoyl-8-[3-isopropyl-amino-2-hydroxy-propoxy]-1,2,3,4-tetrahydroquinoline | 7.0 ± 0.4 | 9.7 ± 0.8 | 12.4 ± 0.8 | 18.0 ± 1.0 |
| Procaine amide (Comparison substance) | 4.0 ± 0.3 | 5.4 ± 0.5 | 7.2 ± 0.3 | 9.6 ± 0.7 |
| Lidocaine (Comparison substance) | 4.3 ± 0.4 | 6.0 ± 0.6 | 8.0 ± 0.9 | 10.4 ± 0.7 |
| Ajmaline (Comparison substance) | 3.9 ± 0.2 | 5.1 ± 0.4 | 7.0 ± 0.7 | 8.6 ± 0.9 |

TABLE 2

| Substances | ED (mg/kg) | |
|---|---|---|
| | intravenous | intraduodenal |
| 1-Nicotinyl-8-[3-isopropyl-amino-2-hydroxy-propoxy]-1,2,3,4-tetrahydroquinoline | 1.5 | 20 |
| Ajmaline (Comparison substance) | 7.0 | 40 |

The invention and its advantages are readily appreciated from the foregoing description. It is apparent that various changes may be made in the compounds, their synthesis, their intermediates, their compositions, their dosage forms, their mode of administration and their use without departing from the spirit or scope of the invention or sacrificing its material advantages. The hereinbefore-described aspects are merely illustrative of preferred embodiments of the invention.

What is claimed is:

1. A pharmacologically-active and physiologically-acceptable compound of the formula

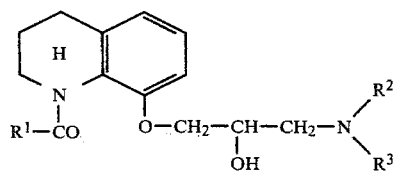

wherein
$R^1$ is lower alkyl, heteroaryl (having 4 or 5 ring carbon atons and 1 ring hereto atom selected from the group consisting of nitrogen, oxygen and sulfur), phenyl or substituted phenyl (any substituent of which is, independently, a member selected from the group consisting of lower alkyl, lower alkoxy, halo and trifluoromethyl), $R^2$ is —H, lower alkyl or, together with $R^3$ and the nitrogen atom to which both are bound, a 5-membered or 6-membered ring having at most one further ring hetero-atom grouping (selected from the group consisting of —O—, —S— and —NH—), and $R^3$ is —H, lower alkyl or, together with $R^2$ and the nitrogen atom to which both are bound, a 5-membered or 6-membered ring having at most one further ring hetero-atom grouping (selected from the group consisting of —O—, —S— and —NH—), or a physiologically-acceptable acid-addition salt thereof.

2. A compound according to claim 1 wherein $R^1$ has from 1 to 5 carbon atoms when it is alkyl, substituted phenyl is mono, di- or tri-substituted, and lower alkyl and lower alkoxy substituents otherwise have from 1 to 3 carbon atoms.

3. A pharmacologically-active and physiologically-acceptable 1-(carboxylic acid)acyl-8-[2-hydroxy-3-(substituted or unsubstituted)aminopropoxy]-1,2,3,4-tetrahydroquinoline according to claim 1 of the formula

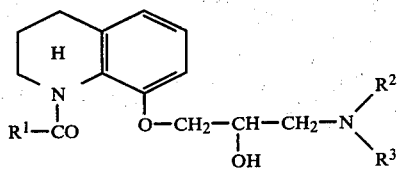

(I)

wherein
- R¹ is lower alkyl, phenyl, phenyl mono-, di- or trisubstituted with lower alkyl, lower alkoxy, halo and/or trifluoromethyl, or thienyl, furyl, pyrrolyl or pyridyl,
- R² is —H, lower alkyl or, together with R³ and the nitrogen atom to which both are bound, 1-piperidinyl, 1-piperazinyl, morpholino, 1-imidazolidinyl or 1-pyrrolidinyl, and
- R³ is —H, lower alkyl or, together with R² and the nitrogen atom to which both are bound, 1-piperidinyl, 1-piperazinyl, morpholino, 1-imidazolidinyl or 1-pyrrolidinyl, or a physiologically-acceptable acid-addition salt thereof.

4. A compound according to claim 2 or claim 3 wherein
- R² is alkyl with from 1 to 4 carbon atoms and
- R³ is alkyl with from 1 to 4 carbon atoms.

5. A compound according to claim 2 or claim 3 wherein R² is —H and R³ is isopropyl or tert.-butyl.

6. A compound according to claim 3 wherein R¹ is alkyl with 1 to 5 carbon atoms, pyridyl, furyl, thienyl, phenyl, trichlorophenyl, chlorophenyl or alkylphenyl having 1 to 3 carbon atoms in the alkyl moiety.

7. A compound according to claim 3 wherein
- R² is —H, alkyl with from 1 to 4 carbon atoms or, together with R³ and the nitrogen atom to which both are bound, 1-piperidinyl, 1-pyrolidinyl or morpholino,
- R³ is —H, alkyl with from 1 to 4 carbon atoms or, together with R² and the nitrogen atom to which both are bound, 1-piperidinyl, 1-pyrolidinyl or morpholino.

8. A compound according to claim 1 wherein any halo substituent of substituted phenyl is chloro or fluoro.

9. A compound according to claim 3 which is 1-nicotinoyl-8-[3-isopropylamino-2-hydroxypropoxy]-1,2,3,4-tetrahydroquinoline or a pharmaceutically-acceptable acid-addition salt thereof.

10. A compound according to claim 3 which is 1-benzoyl-8-[3-morpholino-2-hydroxypropoxy]-1,2,3,4-tetrahydroquinoline or a pharmaceutically-acceptable acid-addition salt thereof.

11. A pharmaceutical formulation useful for treating cardiac arrhythmia and/or hypertension and which has, per unit dose, an effective amount of a tetrahydroquinoline according to claim 1 or of a pharmaceutically-acceptable acid-addition salt thereof, in addition to pharmaceutically-acceptable excipient and/or additive.

12. A pharmaceutical formulation according to claim 11 which further comprises one or more other pharmaceutically-active substances.

13. A pharmaceutical formulation according to claim 12 wherein the other pharmaceutically-active substance or substances are selected from the group consisting of a sedative, vasodilator, diuretic agent, hypotensive agent, cardiotonic agent, α-adrenergic blocking agent, β-adrenergic blocking agent, catechol amine and sympathomimetic agent.

14. A pharmaceutical formulation (useful for treating cardiac arrhythmia) which has, per unit dose, from 0.1 to 50 mg of a tetrahydroquinoline accordng to claim 1 or of a pharmaceutically-acceptable acid-addition salt thereof, in addition to pharmaceutically-acceptable excipient and/or additive.

15. A process for treating cardiac arrhythmia and/or hypertension which comprises administering an effective amount of a compound according to claim 1 or of a physiologically-acceptable acid-addition salt thereof to a patient afflicted with at least one of these conditions.

16. A process according to claim 15 for treating cardiac arrhythmia.

17. A process for treating cardiac arrhythmia and/or hypertension which comprises administering a daily dose of from 0.001 to 1 mg per kilogram of body weight of a compound according to claim 1 or of a physiologically-acceptable acid-addition salt thereof to a patient afflicted with at least one of these conditions.

* * * * *